US010371962B2

(12) United States Patent
Drobe et al.

(10) Patent No.: US 10,371,962 B2
(45) Date of Patent: Aug. 6, 2019

(54) SYSTEM AND METHOD FOR REAL TIME SEGMENTATION

(71) Applicant: ESSILOR INTERNATIONAL (COMPAGNIE GENERALE D'OPTIQUE), Charenton le Pont (FR)

(72) Inventors: Bjorn Drobe, Singapore (SG); Celine Carimalo, Singapore (SG)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 653 days.

(21) Appl. No.: 14/376,162

(22) PCT Filed: Feb. 11, 2013

(86) PCT No.: PCT/EP2013/052700
§ 371 (c)(1),
(2) Date: Aug. 1, 2014

(87) PCT Pub. No.: WO2013/117766
PCT Pub. Date: Aug. 15, 2013

(65) Prior Publication Data
US 2014/0368790 A1 Dec. 18, 2014

(30) Foreign Application Priority Data

Feb. 10, 2012 (EP) .................................... 12305146

(51) Int. Cl.
G06F 17/50 (2006.01)
G02C 7/02 (2006.01)
(Continued)

(52) U.S. Cl.
CPC ........... G02C 7/027 (2013.01); G02C 13/003 (2013.01); G06F 17/50 (2013.01); G06F 19/325 (2013.01); G06Q 10/08 (2013.01)

(58) Field of Classification Search
CPC ............ G06F 9/54; G06F 17/50; A61B 3/103
(Continued)

(56) References Cited

U.S. PATENT DOCUMENTS 8,447,573 B2 5/2013 Allione et al.
8,690,323 B2 4/2014 Hatanaka
(Continued)

FOREIGN PATENT DOCUMENTS

CN 1971607 8/2012
EP 1 752 815 2/2007
(Continued)

OTHER PUBLICATIONS

P. Rosales, Customized computer models of eyes with intraocular lenses. (Year: 2007).*

(Continued)

Primary Examiner — Lechi Truong
(74) Attorney, Agent, or Firm — Young & Thompson

(57) ABSTRACT

A system and method for updating a generic ophthalmic lens design is described. The method includes the steps of selecting a generic ophthalmic lens design from a generic ophthalmic lens design database and receiving, over a data-communication network, lens order data associated with at least one individual lens wearer. The method also includes the steps of creating, using the generic ophthalmic lens design and the lens order data, at least one customized ophthalmic lens design being customized for the respective at least one individual lens wearer and updating the generic ophthalmic lens design in the generic ophthalmic lens design database using the at least one customized ophthalmic lens design.

15 Claims, 3 Drawing Sheets

(51) Int. Cl.
*G06Q 10/08* (2012.01)
*G02C 13/00* (2006.01)
*G06F 19/00* (2018.01)

(58) Field of Classification Search
USPC .............................. 351/200; 719/310; 703/13
See application file for complete search history.

(56) References Cited

U.S. PATENT DOCUMENTS

| | | | |
|---|---|---|---|
| 2001/0033361 A1* | 10/2001 | Edwards | G02C 7/02 |
| | | | 351/159.74 |
| 2002/0176052 A1* | 11/2002 | Ueno | G02C 13/003 |
| | | | 351/245 |
| 2003/0007123 A1* | 1/2003 | Broderick | G02C 7/046 |
| | | | 351/159.74 |
| 2004/0075809 A1* | 4/2004 | Wildsmith | G05B 19/4097 |
| | | | 351/159.74 |
| 2004/0246440 A1* | 12/2004 | Andino | A61B 3/0025 |
| | | | 351/159.74 |
| 2009/0125137 A1 | 5/2009 | Allione et al. | |
| 2011/0043754 A1 | 2/2011 | Hatanaka | |
| 2012/0287405 A1 | 11/2012 | Mousset et al. | |
| 2013/0124159 A1* | 5/2013 | Chen | G06T 5/006 |
| | | | 703/2 |
| 2013/0218533 A1 | 8/2013 | Allione et al. | |
| 2015/0061990 A1* | 3/2015 | Toner | G06F 3/013 |
| | | | 345/156 |

FOREIGN PATENT DOCUMENTS

| | | |
|---|---|---|
| EP | 2 273 306 | 1/2011 |
| EP | 2 325 618 | 5/2011 |
| JP | 2009-020536 A | 1/2009 |
| JP | 2009-505128 A | 2/2009 |
| WO | 2007/017766 A2 | 2/2007 |
| WO | 2009/133887 A1 | 11/2009 |

OTHER PUBLICATIONS

International Search Report dated Sep. 9, 2013, corresponding to PCT/EP2013/052700.
China Office Action dated Jun. 30, 2016, with English Translation; Application No. 201380009021.3.
English translation of Japanese Office Action issued in Application No. 2014-556095, dated Jun. 8, 2017.

* cited by examiner

|   |      |
|---|------|
| P | 5.1° |
| W | 9°   |
| V | 8mm  |

300

|   | CL1   | CL2   | CL3   | ... | CLN-2  | CLN-1 | CLN    | CLN+1  | CLN+2  |
|---|-------|-------|-------|-----|--------|-------|--------|--------|--------|
| P | 5.1°  | 5.0°  | 4.3   | ... | .5°    | 4.5°  | 3.8°   | 5.5°   | 5.6°   |
| W | 9°    | 8.7°  | 7.    | ... | .8°    | 8.9°  | 9.1°   | 9.8°   | 9.5°   |
| V | 8mm   | 7.6mm | 9.1mm | ... | 9.3mm  | 7mm   | 7.8mm  | 9.2mm  | 6.7mm  |

N MEMBER STATISTICAL GROUP

FIG. 3

SYSTEM AND METHOD FOR REAL TIME SEGMENTATION

BACKGROUND OF THE INVENTION

The present invention relates to the field of ophthalmic lens design. More specifically, the present invention relates to a system and method for real time updating of a generic (or segmented) lens design.

DESCRIPTION OF THE RELATED ART

Modern ophthalmic lens design includes a number of processes for producing a wide variety of lens types. These types of lenses include both personalised lenses, which are tailor-made for an individual wearer, and segmented or generic lenses, which relate to lenses having a number of characteristics that are suited to a wearer group, the individuals of which group share a certain number of physiological and behavioural similarities. A segmented lens designed for a particular group will typically need to be customised in order to meet the particular needs of an individual.

In some cases, segmented lenses are designed to meet the anatomic and ergonomic needs of an average ethnic wearer group, such as Indians, Korean or Asian Chinese. For example, in terms of ocular anatomy, the eye length of a typical Asian eye is relatively long. Moreover, the centre of rotation of an Asian eye is further away from the eye lens and the optical axis of an Asian eye tends to sweep over a broader area. In terms of facial anatomy, Asian wearers tend to have less pronounced facial profiles and nose bridges, both of which features will have a direct impact on how frames sit on their faces. The position of a frame impacts on the relative position of the lens to the eye, and therefore has a direct impact on the optical function of the lens.

Furthermore, in terms of ergonomics, Asian wearers tend to move their head closer to objects when reading, which requires a higher degree of convergence, and so a higher inset value is needed.

The characteristics of these segmented lenses are often the result of lengthy studies performed on a sample of the relevant wearer group. Current methods of designing segmented lenses therefore suffer from significant disadvantages.

One such disadvantage is that the sample data are only representative of the location where they have been collected. For example, Asian Chinese data obtained in Singapore may not be representative of data relating to Chinese lens wearers living in Vancouver, Canada. Moreover, these data sets are only valid at one period of time and therefore do not account for changes of the measurement parameters over time (e.g. a change in fashion that leads people to wear smaller frames with lower pantoscopic tilts).

SUMMARY OF THE INVENTION

In order to solve the problems associated with the prior art, the present invention provides a method of updating a generic ophthalmic lens design, which method comprises the steps of: selecting a generic ophthalmic lens design from a generic ophthalmic lens design database; receiving, over a data-communication network, lens order data associated with at least one individual lens wearer; creating, using the generic ophthalmic lens design and the lens order data, at least one customised ophthalmic lens design being customised for the respective at least one individual lens wearer; and updating the generic ophthalmic lens design in the generic ophthalmic lens design database using the at least one customised ophthalmic lens design.

Preferably, the generic ophthalmic lens design includes generic lens design parameters, the at least one customised ophthalmic lens design includes customised lens design parameters, and the generic lens design parameters are determined as a result of statistical analysis performed on at least one customised lens design parameter of a first group of customised ophthalmic lens designs, and wherein the step of updating the generic ophthalmic lens design further comprises the steps of: adding the at least one customised ophthalmic lens design to the first group of customised ophthalmic lens designs to form a second group of customised ophthalmic lens designs; and performing statistical analysis on at least one customised lens design parameter of the second group of customised ophthalmic lens designs.

Preferably, the method further comprises: removing at least one customised ophthalmic lens design from the second group of customised ophthalmic lens designs before performing statistical analysis.

Preferably, the step of performing the statistical analysis on at least one customised lens design parameter of the second group of customised ophthalmic lens designs further includes the step of: performing different types of statistical analysis on different customised lens design parameters of the second group of customised ophthalmic lens designs.

Preferably, the second group of customised ophthalmic lens designs is formed of ophthalmic lens designs customised for individual lens wearers of a specific geographical area or individuals who are clients of a specific eye care professional.

Preferably, the lens order data is received from a plurality of remote locations over an encrypted data-communication channel.

The present invention further provides an ophthalmic lens design system for updating a generic ophthalmic lens design, the system comprises processing means arranged to: select a generic ophthalmic lens design from a generic ophthalmic lens design database; receive, over a data-communication network, lens order data associated with at least one individual lens wearer; create, using the generic ophthalmic lens design and the lens order data, at least one customised ophthalmic lens design being customised for the respective at least one individual lens wearer; and update the generic ophthalmic lens design in the generic ophthalmic lens design database using the at least one customised ophthalmic lens design.

Preferably, the generic ophthalmic lens design includes generic lens design parameters, the at least one customised ophthalmic lens design includes customised lens design parameters, and the generic lens design parameters are determined as a result of statistical analysis performed on at least one customised lens design parameter of a first group of customised ophthalmic lens designs, and wherein the ophthalmic lens design system further comprises processing means arranged to: add the at least one customised ophthalmic lens design to the first group of customised ophthalmic lens designs to form a second group of customised ophthalmic lens designs; and update the generic ophthalmic lens design by performing statistical analysis on at least one customised lens design parameter of the second group of customised ophthalmic lens designs.

Preferably, the ophthalmic lens design system further comprises processing means arranged to: remove at least one customised ophthalmic lens design from the second group of customised ophthalmic lens designs before performing the statistical analysis.

Preferably, the ophthalmic lens design system further comprises processing means arranged to: perform different types of statistical analysis on different customised lens design parameters of the second group of customised ophthalmic lens designs.

Preferably, the first and second groups of customised ophthalmic lens designs are formed of ophthalmic lens designs customised for individual lens wearers of a specific geographical area or individual lens wearers who are clients of a specific eye care professional.

Preferably, the ophthalmic lens design system further comprises: a plurality of measurement devices located in different geographical locations, each measurement device being arranged to measure at least one parameter related to a particular wearer; and a plurality of lens order data generating devices located in different geographical locations, each lens order data generating device being arranged to process the at least one parameter and generate lens order data associated with at least one individual lens wearer, and to send the lens order data, over the data-communication network.

Preferably, communication of the lens data, over the data-communication network, is performed using an encrypted data-communication channel.

The present invention also provides a networked data processing apparatus for updating a generic ophthalmic lens design, the networked data processing apparatus comprising processing means for performing the steps of the above method.

The present invention further provides a computer program product for a data-processing device, the computer program product comprising a set of instructions which, when loaded into the data-processing device, causes the device to perform the steps of the above method.

As will be appreciated, the present invention provides several advantages over the prior art. For example, because the system of the present invention can use a number of sources of data for updating a segmented lens design, it has increased flexibility over prior art systems. This increase in flexibility allows systems in accordance with the present invention to produce segmented lenses which are better suited to a wearer group, regardless if that group represents citizens of a global region (e.g. Asia), residents of a given country (e.g. China), or customers of a specific eye care professional, or group of eye care professionals. Moreover, the ability to update generic lens designs in real time (i.e. as new lens designs are created in respect of new lens orders) allows the system to be much more responsive, and thereby to more effectively track the physiological and/or behavioural changes in a given population.

BRIEF DESCRIPTION OF THE DRAWING FIGURES

Further advantages of the present invention will become apparent upon reading the detailed description set out below, in conjunction with the accompanying drawings, in which:

FIG. 3 is a simplified diagram of a plurality of specific lens designs in accordance with one example of the present invention.

DETAILED DESCRIPTION OF THE INVENTION

In the following detailed description of several embodiments of the present invention, the term "ophthalmic lens" is used to describe any type of lens related to the eye and includes, but is not limited to, spectacle lenses, contact lenses and intraocular lenses.

The expression "ophthalmic lens design" is used to describe the data allowing for the creation of a physical ophthalmic lens. An ophthalmic lens design can include "lens design parameters", which are a set of parameters relating to the physical features of a lens and/or the optical function of a lens.

The expression "generic ophthalmic lens design" is used to describe the data allowing for the creation of a physical generic ophthalmic lens, which generic ophthalmic lens, also known as a segmented lens, has a number of characteristics that are suited to a wearer group, the individuals of which group share a certain number of physiological and behavioural similarities. Typically, a segmented lens relates to an ophthalmic lens designed for a relatively small group (or "segment" of a larger group); whereas a generic lens relates to an ophthalmic lens suitable for use by a relatively large group. A generic ophthalmic lens design can include "generic lens design parameters", which are a set of parameters relating to the physical features of a generic lens and/or the optical function of a generic lens.

The expression "customised ophthalmic lens design" is used to describe the data allowing for the creation of a physical ophthalmic lens which is customised for an individual wearer. The customised ophthalmic lens design can include "customised lens design parameters", which are a set of parameters relating to the physical features of a customised lens and/or the optical function of a customised lens.

Finally, the expression "lens order data" is used to describe information relating to a lens order, which information can include, amongst other information, the name of the lens wearer, the lens wearer's prescription, the type of lens, the name of an eye care professional associated with the lens wearer and at least one of the physical features of a lens and/or the optical function of a lens. Other information which can be included in lens order data include fitting parameters, frame dimensions, indexes, coatings, personalization parameters (e.g. wearing conditions, eye center or rotation, head/eye movements).

Figure 1:
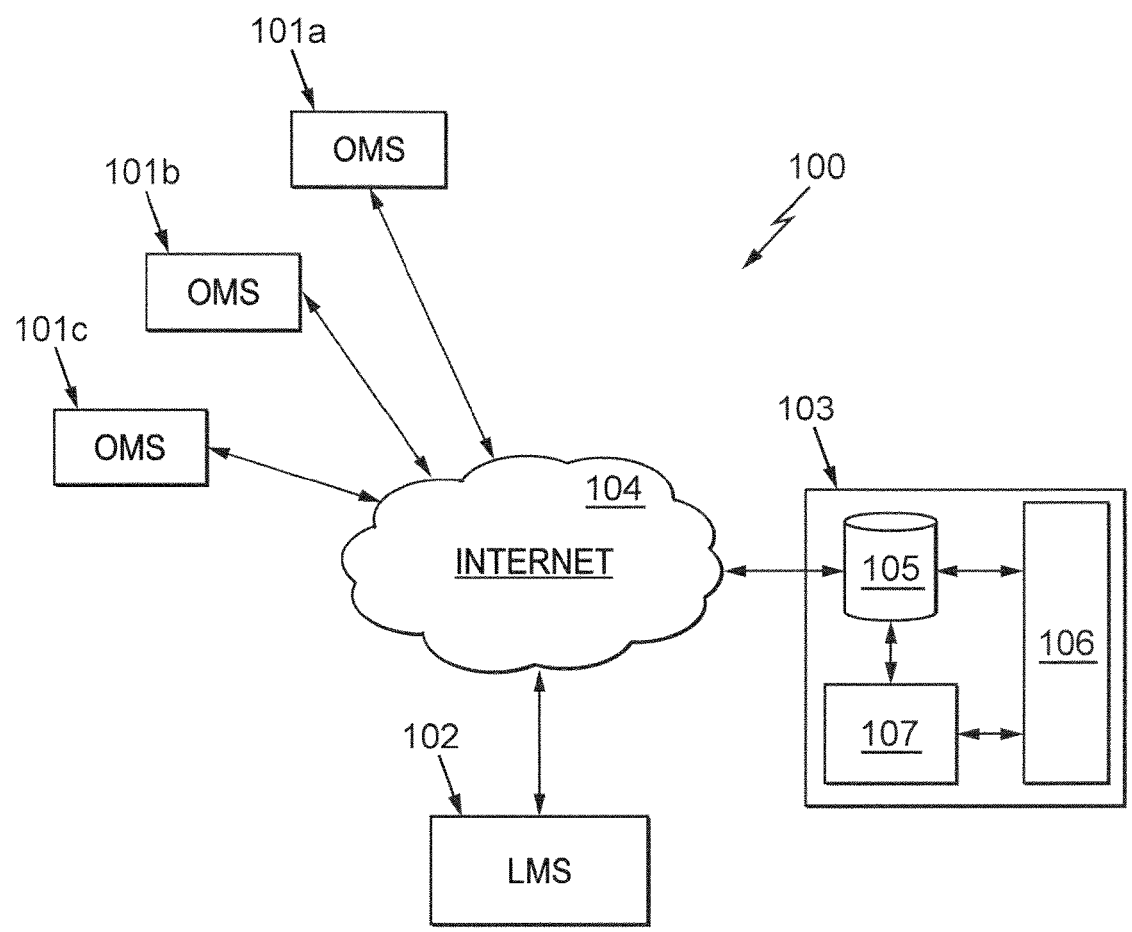
FIG. 1 is a functional block diagram of a system which can be used in accordance with one embodiment of the present invention.

FIG. 1 is a functional block diagram of a system 100 in accordance with an embodiment of the present invention. In particular, the system comprises a number of Ordering Management Systems (OMS) 101a, 101b, 101c, which receive orders for the creation of lenses, each order having lens order data associated therewith. In some embodiments of the invention, the OMS 101a, 101b, 101c can form part of a centralised computer system which collects order information from eye care professionals, such as opticians and/or ophthalmologists. In these embodiments, eye care professionals can logon to a centralised OMS system and upload information relating to a specific lens order. In alternate embodiments, each OMS 101a, 101b, 101c can be situated on the premises of a particular eye care professional. In these alternate embodiments, an eye care professional can input information directly into the OMS 101a, 101b, 101c. As will be appreciated, other OMS arrangements are possible, such as having OMS server software implemented in a network server, and having OMS client software installed on computer systems used by individual eye care professionals. In the above embodiments, the OMS 101a, 101b, 101c use the information input in to the system in order to produce lens order data relating to a lens order for a given lens wearer. The information input into the OMS can be collected automatically by any number of ophthalmic measurement devices and/or input manually by an eye care professional. Each OMS 101a, 101b, 101c can be located in a different physical location (i.e. different neighbourhoods, cities, countries, or continents).

The OMS 101a, 101b, 101c of FIG. 1 are connected via a data communication network to a Laboratory Management System (LMS) 102, which LMS 102 manages information transfer relating to the creation of lenses. Known Laboratory Management Systems can manage the implementation of the various manufacturing steps of the lens, or can manage a part of these.

The OMS 101a, 101b, 101c and LMS 102 can be connected via the Internet 104. Preferably, communication between the OMS 101a, 101b, 101c and LMS 102 is encrypted in order to secure the lens order data. The OMS 101a, 101b, 101c and the LMS 102 are also connected, via a data communication network, to a Segmented Lens Database (SLD) 103. The SLD 103 comprises a memory 106 for storing a number of generic ophthalmic lens designs, each of which comprising a plurality of generic lens design parameters relating to the physical features of a generic lens and/or the optical function of a generic lens. The SLD 103 also includes a server 105 which is arranged to access the memory 106 in order to provide generic lens designs to the LMS 102 over the Internet 104. Finally, the SLD 103 also includes a processor 107 which is connected to the server 105 and the memory 106, which processor 107 is arranged to receive new customised lens designs from the server 105 and update the generic lens designs in the memory using statistical analysis, as described below.

Figure 2:
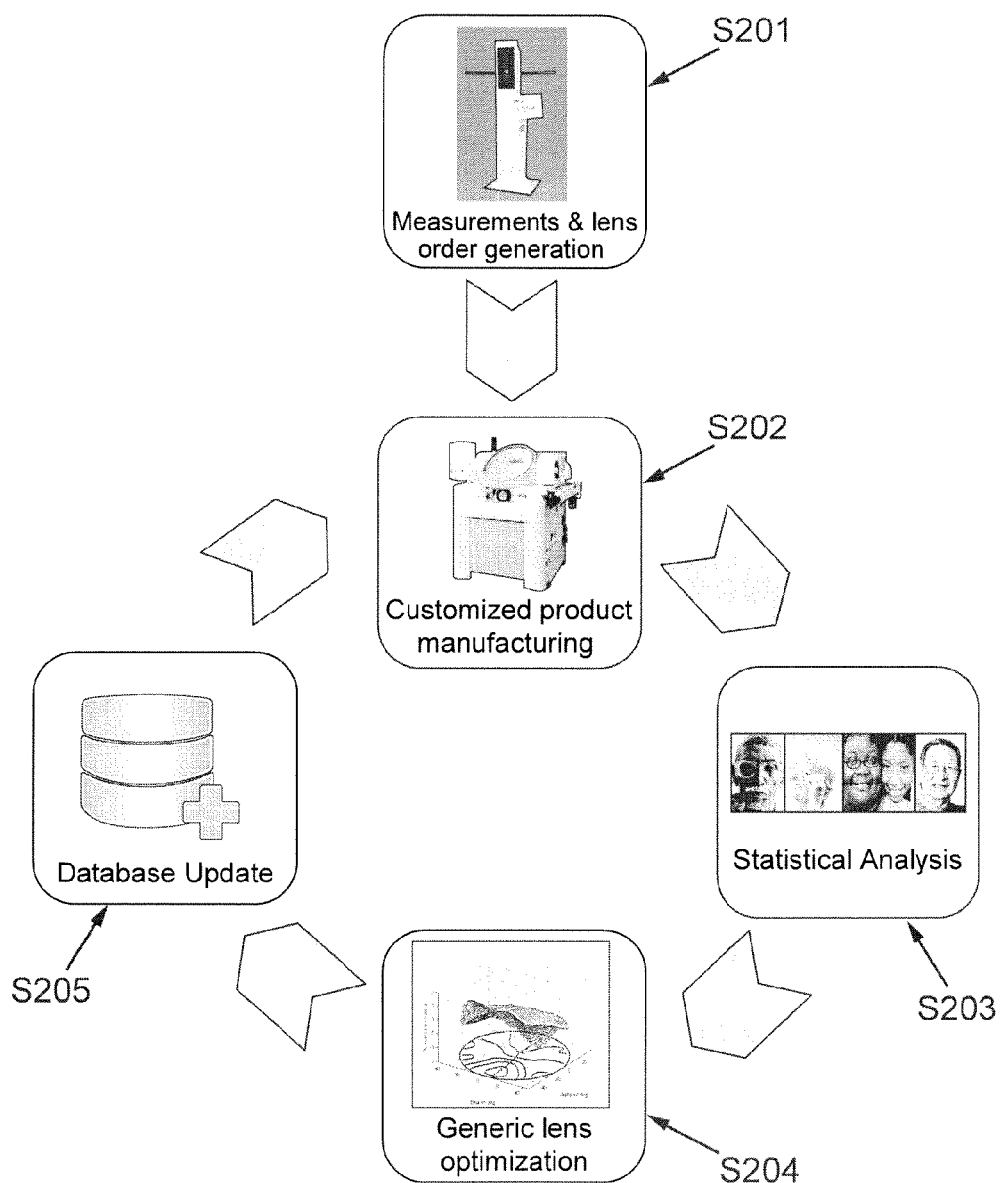
FIG. 2 is a functional block diagram of a method in accordance with one embodiment of the present invention.

With reference to FIGS. 1 and 2, a method of manufacturing a lens in accordance with the system and method of the present invention is described below. In the measurement and lens order generation step S201, a number of measurements can be taken by an eye care professional, and a lens order can be generated at OMS 101a, for example. The lens order will generally comprise a plurality of lens order data, which can include, amongst other information, the name of the lens wearer, the lens wearer's prescription, the type of lens, the name of an eye care professional associated with the lens wearer and at least one of the physical features of a lens and/or the optical function of a lens.

In the customized product manufacturing step S202, the lens order data is sent to the LMS 102, which accesses the SLD 103 in order to choose a segmented lens which is suitable for the particular lens order. While the present embodiment is being described with reference to the selection of a segmented lens, the SLD 103 could instead select a generic lens, which, as described above, is simply a lens which is suitable for a larger group of wearers.

Lens designs are typically embodied in an electronic file of a particular and predefined format. Many known file types, such as Extensible Markup Language (XML) files, are suitable for use with the present invention. Lens design files in accordance with the present invention can include a number of lens design parameters, as defined above. Alternatively, lens design files can comprise a number of lens design parameters relating to a physical lens (e.g. a particular segmented lens), together with a number of modifications which need to be made to the physical lens in order for it to be optimised for use by a particular individual.

Once a segmented lens design (i.e. a segmented lens design file) is chosen from the memory 106, it is sent to the LMS 102. Using the segmented lens design and the lens order data, the LMS 102 produces a customised lens design which it will use to modify the physical segmented lens. The skilled reader will understand that a large number of possible customisation steps are possible in this process. For example, product customisation can include calculating, using the lens order data and the customised lens design, a set of required modifications which need to be made to the segmented lens in order for it to be customised for the lens wearer in respect of which the lens order data have been generated. Such types of calculation will be apparent to the skilled reader and, for the sake of brevity, will not be described here.

Once the customised lens design is produced, either by way of producing a customised lens design including a complete set of customised lens design parameters, or simply by appending the required modifications to the segmented lens design, the actual customised lens can be manufactured.

The customised lens can be manufactured by lens making machines which form part of the LMS 102, or which are connected to (or in contact with) the LMS 102. In one embodiment, the LMS 102 is arranged to convert a customised lens design (i.e. the contents of a customised lens design file) into a set of machine instructions for modifying a segmented lens, which segmented lens corresponds to the segmented lens design chosen in relation to the lens order data generated in step S201.

In another embodiment, the LMS 102 is arranged to convert the segmented lens design (i.e. the contents of the segmented lens design file), together with any modifications calculated (as describes above), into a set of machine instructions for modifying the segmented lens (which corresponds to the segmented lens design) into a customised lens. The machine instructions are then used by the lens making machines in order to produce the customised lens using the segmented lens. Once produced, the customised lens is sent to the eye care professional and the customised lens design which was used to create the customised lens is sent to the SLD 103.

In step S203, the SLD 103 receives a customised lens design which it adds to a relevant set of customised lens designs, as described below. In step S204, the SLD 103 uses the results of the statistical analysis performed in step S203 to optimize a relevant generic (or segmented) lens design, as also described below.

Finally, in step S205, the generic lens design database S205 is updated. The updated contents of the database are then available to be used in a subsequent customised product manufacturing step S202. In some embodiments of the invention, steps S203, S204 and S205 can be executed once a given number of new lens orders are received. For example, in one embodiment of the invention, steps S203, S204 and S205 are executed once for every 1000 new lens orders received. As will be appreciated, the number of new lens orders required before steps S203, S204 and S205 are triggered can vary.

In reference to FIGS. 2 and 3, a detailed example of the operation of the SLD 103 in regard to the execution of step S203, S204 and S205 is described below. In this example, the SLD 103 provides a unique generalist Progressive Addition Lens (PAL) design to a single eye care professional who provides customized PALs to his customers.

In the simplified example of FIG. 3, a customised lens design 300 comprises a plurality of lens design parameters, namely pantoscopic tilt P, wrap angle W and vertex distance V. As will be appreciated, typical lens designs comprise many more parameters. For the sake of simplicity however, and with a view to setting out an illustrative and non-limiting example of the technical features of the present invention, the lens design of the example of FIG. 3 merely comprises the abovementioned three variables.

In step S201, lens order data is generated in regard to a specific customer, as described above. The lens order will generally comprise a plurality of lens order data, which can include, amongst other information, the name of the lens wearer, the lens wearer's prescription, the type of lens, the name of an eye care professional associated with the lens wearer and at least one of the physical features of a lens and/or the optical function of a lens.

In step S202, the lens order data is analysed and a segmented lens design may be chosen from the SLD 103. The contents of the lens order data will determine whether a particular wearer, in respect of whom the lens order data has been generated, is well suited to a particular segmented lens. Once the segmented lens design is selected, it is used, together with the lens order data, to create a customised lens design 300. As described above, the customised lens design can comprise a particular segmented lens design, together with a number of modifications which need to be made to the segmented lens design in order to arrive at the customised lens design.

In the example of FIG. 3 however, the customised lens design 300 comprises a complete set of customised lens design parameters, namely pantoscopic tilt P, wrap angle W and vertex distance V. In this example the customised lens design 300 comprises a P value of 5°, a W value of 9° and a V value of 8 mm.

In order to begin step S203, the customised lens design is sent from the LMS 102 to the SLD 103. The processor 107 is arranged to perform statistical analysis on a number of customised lens designs CL, each of which are stored in the memory 106.

The initial values for the customised lens design CL set can be chosen using any number of known techniques. For example, the initial values could be based on using generic designs sold by the eye care professional that is making the order. Alternatively, the initial set of values could be generated using prior art methods of relying on the results of studies performed on population samples. In the present example however, the memory 106 contains a number of customised lens designs CL2 to CLN+2, to which set will be added customised lens design 300, hereinafter referred to as CL1.

In the present example, step S203 is performed on a given number N of the latest customised lens designs (i.e. CL1 to CLN). As each new lens design is added to the set, the $N^{th}$ customised lens design is removed, and the $N^{th}-1$ customised lens design becomes the $N^{th}$ lens design. In this manner, the statistical analysis performed in step S203 is performed on the last N customised lens designs received from the LMS 102. While this example provides particularly advantageous effects in terms of tracking the evolution of the requirements of a group of lens wearers, other variations will be apparent to the skilled reader. For example, provided that enough storage space is available in memory 106, all customised lens designs could be used each time a statistical analysis is performed.

In one embodiment of the present invention, a step of pre-analysis of the data is performed in order to discard customised lens designs which include customised lens design parameters that are outside the bounds of statistical relevance. In the example of FIG. 3, the customised lens design CLN-2 comprises a P value of 0.5° and a W value of 0.8°, which is outside +/-3 standard deviations of the average value. Such an anomaly could be a result of erroneous lens order data, or it could simply be that a particular lens wearer requires a customised lens design comprising extreme parameters.

In any event, in the example of FIG. 3, CLN-2 could be removed in a pre-analysis step, thereby increasing the statistical relevance of the statistical analysis step by performing the analysis on the remaining data. Other examples of pre-analysis steps are also within the scope of the invention.

In the example of FIG. 3, the customised lens designs which remain in a statistically relevant group after any pre-analysis is performed will then be analyzed using at least one statistical method. Using several different types of statistical analysis is also within the scope of the invention. For example, in accordance with the example shown in FIG. 3, it may be advantageous to perform a different type of statistical analysis on each of the customised lens design parameters, namely pantoscopic tilt P, wrap angle W and vertex distance V. Thus, it may be advantageous to calculate the mode (i.e. the value that occurs the most often in a data set) of the pantoscopic tilt P values for the N member statistical group. It may also, for example, be advantageous to not calculate the mode of the wrap angle W values, but rather the median (i.e. the numerical value which separates the higher half of a sample from the lower half) of these values. Similarly, the most statistically relevant analysis of the vertex distance V could simply be to find its average value. The above are non-limiting examples of the flexibility and versatility of the analyzing means of the present invention. It will be understood that other examples of statistical analysis will also be included within the scope of the present invention.

Accordingly, once the processor 107 has identified the statistical group which is to be analyzed, the customised lens design parameter (P, W or V) can be analyzed using a single analysis method, or alternatively, each customised lens design parameter can be analyzed using an independent analysis method. Moreover, in the example shown in FIG. 3, two customised lens design parameters could be analyzed using the same method, and the third could be analyzed using a second method. The skilled reader will appreciate that, given the fact that customized lens designs can potentially comprise several hundred customized lens design parameters, and that any combination of these can be analyzed using various methods, the flexibility and versatility of the present invention will allow complex statistical analysis of customized lenses.

Once the statistical analysis has taken place in step S203, the results will be used by the processor 107 to modify a segmented (or generic) lens design such that it reflects some facet of the results. For example, the segmented lens design associated with the customized lens designs shown in FIG. 3 could be modified by simply using the mode value of the pantoscopic tilt P parameter in the customized lens design of the statistically relevant group, the median value of the wrap angle W parameter in the customized lens design of the statistically relevant group, and the average value of the vertex distance V parameter in the customized lens design of the statistically relevant group.

Alternatively, the parameter values of the non-modified segmented lens design and the parameter values which result from the statistical analysis could be combined using a weighting function in order to give more or less weight to the results obtained by analyzing customized lens designs. This feature of the invention allows some degree of control over how closely the segmented lens design would track the requirements of a give group of wearers.

Once the generic lens is optimized in step S204, the generic lens design database S205 is updated using the optimized segmented lens design. This updated segmented lens design can be used by lens manufacturers to modify the segmented lens that they produce, after which point the optimized segmented lens design can be made available on the server 105 of the SLD 103, in order to be used by the LMS 102 in future customized product manufacturing S202.

Alternatively, the optimized segmented lens design can be stored in the database and used by lens manufacturers to track changes in the ophthalmic needs (i.e. segmented lens designs) of a group of their customers. By doing so, it is possible for the lens manufacturer to produce a new segmented lens once the difference between the parameters of the segmented lens they are currently producing and the parameters of the optimized segmented lenses they are storing in the database reaches a predetermined threshold. Once the threshold is reached, the lens manufacturer can decide to produce a new segmented lens in accordance with an optimized segmented lens design generated using the present invention. The optimized segmented lens design could then be used in further customized product manufacturing steps S202.

Thus, the flexibility, versatility and responsiveness of the system and method of the present invention leads to the production of segmented lenses which are better suited to a wearer group, regardless of whether that group represents citizens of a global region (e.g. Asia), residents of a given country (e.g. China), or customers of a specific eye care professional, or group of eye care professionals. Moreover, the ability to update generic lens designs in real time (i.e. as new lens designs are created in respect of new lens orders) allows the system to rapidly track the physiological and/or behavioural changes in a given population.

The skilled person will realize that steps of various above-described methods can be performed by programmed computers. Accordingly, the above-mentioned embodiments should be understood to cover storage devices containing machine-executable or computer-executable instructions to perform some or all of the steps of the above-described methods. The embodiments are also intended to cover computers programmed to perform the steps of the above-described methods.

The functionality of the elements shown in the Figures can be provided using either dedicated hardware and/or software. The expressions "processing", "processing means" and "processing module" can include, but is not limited to, any of digital signal processor (DSPs) hardware, network processors, application specific integrated circuits (ASICs), field programmable gate arrays (FPGAs), read only memories (ROMs) for storing software, random access memories (RAMs), and non volatile storage.

The invention claimed is:

1. A method of updating in real time a generic ophthalmic lens design, the method comprising steps of:
   selecting a generic ophthalmic lens design from a generic ophthalmic lens design database;
   receiving, over a data-communication network, lens order data associated with at least one individual lens wearer;
   creating, using the generic ophthalmic lens design and the lens order data, at least one customized ophthalmic lens design being customized for the respective at least one individual lens wearer;
   updating, in real time, the generic ophthalmic lens design in the generic ophthalmic lens design database once the generic lens is optimized by statistically analyzing the at least one customized ophthalmic lens design created using the lens order data and the generic ophthalmic lens design before update from the generic ophthalmic lens design database, said real time update of the generic ophthalmic lens design in the generic ophthalmic lens design database being performed before any new customization of a next individual lens wearer to be customized, wherein,
   the generic ophthalmic lens design includes generic lens design parameters,
   the at least one customized ophthalmic lens design includes customized lens design parameters, and
   the generic lens design parameters are determined as a result of statistical analysis performed on at least one customized lens design parameter of a first group of customized ophthalmic lens designs, and wherein the step of updating the generic ophthalmic lens design further comprises the steps of:
   adding the at least one customized ophthalmic lens design to the first group of customized ophthalmic lens designs to form a second group of customized ophthalmic lens designs; and
   performing statistical analysis on at least one customized lens design parameter of the second group of customized ophthalmic lens designs; and
   removing at least one customized ophthalmic lens design from the second group of customized ophthalmic lens designs before performing statistical analysis.

2. The method of claim 1, wherein the step of performing the statistical analysis on at least one customized lens design parameter of the second group of customized ophthalmic lens designs further includes the step of:
   performing different types of statistical analysis on different customized lens design parameters of the second group of customized ophthalmic lens designs.

3. The method of claim 1, wherein the second group of customized ophthalmic lens designs is formed of ophthalmic lens designs customized for individual lens wearers of a specific geographical area or individuals who are clients of a specific eye care professional.

4. The method of claim 1, wherein the lens order data is received from a plurality of remote locations over an encrypted data-communication channel.

5. An ophthalmic lens design system for updating in real time a generic ophthalmic lens design, the system comprising:
   a memory storing a generic ophthalmic lens design database; and
   a processor connected to a data-communication network and connected to the memory storing the generic ophthalmic lens design database, the processor being comprised of computer hardware that executes a set of instructions to cause the computer hardware to:
   i) select a generic ophthalmic lens design from the generic ophthalmic lens design database;
   ii) receive, over the data-communication network, lens order data associated with at least one individual lens wearer;
   iii) create, using the generic ophthalmic lens design and the lens order data, at least one customized ophthalmic lens design being customized for the respective at least one individual lens wearer; and iv) update, in real time, the generic ophthalmic lens design in the generic ophthalmic lens design database once the generic lens is optimized by statistically analyzing the at least one customized ophthalmic lens design created using the lens order data and the generic ophthalmic lens design before update from the generic ophthalmic lens design database, said real time update of the generic ophthalmic lens design in the generic ophthalmic lens design database being performed before any new customization of a next individual lens wearer to be customized, wherein, the generic ophthalmic lens design includes generic lens design parameters, the at least one customized ophthalmic lens design includes customized lens design parameters, and the generic lens design parameters are determined as a result of statistical analysis performed on at least one customized lens design parameter of a first group of customized ophthalmic lens designs, and wherein the ophthalmic lens design system further comprises a further processor connected to the memory storing the generic ophthalmic lens design database, the further processor comprised of a further computer hardware that executes a further set of instructions to cause the further computer hardware to:

add the at least one customized ophthalmic lens design to the first group of customized ophthalmic lens designs to form a second group of customized ophthalmic lens designs; and update the generic ophthalmic lens design by performing statistical analysis on at least one customized lens design parameter of the second group of customized ophthalmic lens designs, and wherein the further processor is arranged to:

remove at least one customized ophthalmic lens design from the second group of customized ophthalmic lens designs before performing the statistical analysis.

6. The ophthalmic lens design system of claim 5, wherein the further processor is s arranged to:

perform different types of statistical analysis on different customized lens design parameters of the second group of customized ophthalmic lens designs.

7. The ophthalmic lens design system of claim 5, wherein the first and second groups of customized ophthalmic lens designs are formed of ophthalmic lens designs customized for individual lens wearers of a specific geographical area or individual lens wearers who are clients of a specific eye care professional.

8. The ophthalmic lens design system of claim 5, further comprising:

a plurality of measurement devices located in different geographical locations, each measurement device being arranged to measure at least one parameter related to a particular wearer; and a plurality of lens order data generating devices located in different geographical locations, each lens order data generating device being arranged to process the at least one parameter and generate lens order data associated with at least one individual lens wearer, and to send the lens order data, over the data-communication network.

9. The ophthalmic lens design system of claim 5, wherein communication of the lens data, over the data-communication network, is performed using an encrypted data-communication channel.

10. The ophthalmic lens design system of claim 5, further comprising:

an ordering management system comprised of further computer hardware connected to the data-communication network, the ordering management system arranged to receive an order for creation of the lens order data associated with the at least one individual lens wearer, wherein the processor is arranged to receive the lens order data from the ordering management system via the data-communication network and to receive the generic ophthalmic lens design from the generic ophthalmic lens design database via the data-communication network, the generic ophthalmic lens design includes generic lens design parameters, the at least one customized ophthalmic lens design includes customized lens design parameters, and the generic lens design parameters are determined as a result of statistical analysis performed on at least one customized lens design parameter of a first group of customized ophthalmic lens designs, and wherein the ophthalmic lens design system further comprises a further processor connected to the memory storing the generic ophthalmic lens design database, the further processor comprised of a further computer hardware that executes a further set of instructions to cause the further computer hardware to:

add the at least one customized ophthalmic lens design to the first group of customized ophthalmic lens designs to form a second group of customized ophthalmic lens designs; and update the generic ophthalmic lens design by performing statistical analysis on at least one customized lens design parameter of the second group of customized ophthalmic lens designs.

11. The ophthalmic lens design system of claim 10, wherein the data-communication network includes the Internet.

12. The ophthalmic lens design system of claim 5, further comprising:

an ordering management system comprised of further computer hardware connected to the data-communication network, the ordering management system arranged to receive an order for creation of the lens order data associated with the at least one individual lens wearer; and a server connected i) to the memory storing the generic ophthalmic lens design database and ii) to the data-communication network, wherein the processor is arranged to receive the lens order data from the ordering management system via the data-communication network and to receive the generic ophthalmic lens design from the generic ophthalmic lens design database via the server and the data-communication network, and wherein the processor updates, in real time, the generic ophthalmic lens design in the generic ophthalmic lens design database via the data-communication network and via the server.

13. The ophthalmic lens design system of claim 12, wherein the data-communication network includes the Internet.

14. A networked data processing apparatus for updating a generic ophthalmic lens design, the networked data processing apparatus comprising processing means including a processor comprised of computer hardware that executes a set of instructions to cause the computer hardware to perform the steps of the method of claim 1.

15. A non-transitory storage medium for a data-processing device, the non-transitory storage medium storing a set of instructions which, when loaded into the data-processing device that includes a processor comprised of computer hardware, causes the computer hardware of the data-processing device to perform the steps of the method of claim 1.

\* \* \* \* \*